United States Patent
Malla

(10) Patent No.: US 12,076,132 B2
(45) Date of Patent: *Sep. 3, 2024

(54) GAS THERAPY SYSTEM

(71) Applicant: Fisher & Paykel Healthcare Limited, Auckland (NZ)

(72) Inventor: Amol Man Malla, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 65 days.

This patent is subject to a terminal disclaimer.

(21) Appl. No.: 17/170,670

(22) Filed: Feb. 8, 2021

(65) Prior Publication Data

US 2021/0259577 A1 Aug. 26, 2021

Related U.S. Application Data

(63) Continuation of application No. 15/576,624, filed as application No. PCT/IB2016/053107 on May 27, 2016, now Pat. No. 10,912,489.

(Continued)

(51) Int. Cl.
*A61B 5/087* (2006.01)
*A61B 5/00* (2006.01)
(Continued)

(52) U.S. Cl.
CPC .......... *A61B 5/0816* (2013.01); *A61B 5/0826* (2013.01); *A61B 5/087* (2013.01);
(Continued)

(58) Field of Classification Search
CPC ......... A61M 2016/003–0042; A61M 2205/15; A61B 5/087–09; A61B 5/0823; A61B 5/0826; A61B 5/7282
See application file for complete search history.

(56) References Cited

U.S. PATENT DOCUMENTS

| 5,551,419 A | 9/1996 | Froehlich et al. |
| 10,912,489 B2 * | 2/2021 | Malla ............ A61B 5/087 |

(Continued)

FOREIGN PATENT DOCUMENTS

| WO | WO 2006/079152 A1 | 8/2006 |
| WO | WO 2010/021556 A1 | 2/2010 |

(Continued)

OTHER PUBLICATIONS

Hernandez et al., "Performance of Nasal Prongs in Sleep Studies; Spectrum of Flow-Related Events," CHEST, vol. 119(2), pp. 442-450 (Feb. 2001).

*Primary Examiner* — Meredith Weare
(74) *Attorney, Agent, or Firm* — Knobbe, Martens, Olson & Bear, LLP

(57) ABSTRACT

A respiratory event determination system can have a controller that determines the presence of a respiratory event. The respiratory event can be a mouth puff event. The controller determines the presence as a function of a sub-window of an expiratory window of the breath. The expiratory window extends between a first time $t_1$ and a second time $t_2$. The sub-window is limited to a portion of the expiratory window. The sub-window can extend between a third time $t_3$ and a fourth time $t_4$. The fourth time $t_4$ can be before the second time $t_2$.

16 Claims, 7 Drawing Sheets

Related U.S. Application Data

(60) Provisional application No. 62/167,821, filed on May 28, 2015.

(51) Int. Cl.
*A61B 5/08* (2006.01)
*A61M 16/00* (2006.01)
*A61M 16/06* (2006.01)
*A61M 16/16* (2006.01)

(52) U.S. Cl.
CPC .......... *A61B 5/4818* (2013.01); *A61B 5/7282* (2013.01); *A61M 16/0066* (2013.01); *A61M 16/0666* (2013.01); *A61M 16/16* (2013.01); A61M 2016/0027 (2013.01); A61M 2016/003 (2013.01); *A61M 16/0051* (2013.01); *A61M 16/026* (2017.08); A61M 2205/15 (2013.01); A61M 2205/3334 (2013.01)

(56) References Cited

U.S. PATENT DOCUMENTS

| | | |
|---|---|---|
| 2007/0068528 A1 | 3/2007 | Bohm et al. |
| 2009/0187082 A1* | 7/2009 | Cuddihy ................ G16H 40/67 |
| | | 600/300 |
| 2010/0292568 A1 | 11/2010 | Droitcour et al. |
| 2011/0259330 A1* | 10/2011 | Jafari .................. A61M 16/024 |
| | | 702/51 |
| 2012/0037159 A1 | 2/2012 | Mulqueeny et al. |
| 2013/0317765 A1 | 11/2013 | Rao et al. |
| 2014/0041656 A1 | 2/2014 | Jourdain et al. |
| 2014/0276168 A1* | 9/2014 | Vissapragada Venkata Satya ...... |
| | | A61B 5/7278 |
| | | 600/529 |

FOREIGN PATENT DOCUMENTS

| | | |
|---|---|---|
| WO | WO 2012/012835 A2 | 2/2012 |
| WO | WO 2013/057635 A1 | 4/2013 |

* cited by examiner

GAS THERAPY SYSTEM

INCORPORATION BY REFERENCE TO ANY PRIORITY APPLICATIONS

Any and all applications for which a foreign or domestic priority claim is identified in the Application Data Sheet as filed with the present application are incorporated by reference under 37 CFR 1.57 and made a part of this specification.

BACKGROUND

Technical Field

The present disclosure generally relates to the determination of respiratory events. More particularly, the present disclosure generally relates to the determination of respiratory events as a function of expiratory portions of breaths.

Description of the Related Art

In patients suffering from obstructive sleep apnea (OSA), muscles that normally keep the upper airway open relax during slumber to the extent that the airway is constrained or completely closed off, a phenomenon often manifesting itself in instances of perceptible cessation of breathing or episodes of snoring. When this blockage of the airway occurs for a period of time, the patient's brain typically recognizes the threat of hypoxia and partially wakes the patient in order to open the airway so that normal breathing may resume. The patient may be unaware of these waking episodes or of associated blockages of the airway, which may occur as many as several hundred times per session of sleep. These partial awakenings or blockages may significantly reduce the quality of the patient's sleep, over time potentially leading to a variety of symptoms, including excessive daytime sleepiness, chronic fatigue, elevated heart rate, elevated blood pressure, weight gain, headaches, irritability, depression and anxiety.

Obstructive sleep apnea is commonly treated with the application of positive airway pressure (PAP) therapy. PAP therapy involves delivering a flow of gas to a patient at a therapeutic pressure above atmospheric pressure that will reduce the frequency and/or duration of apneas, hypopneas, and/or flow limitations. The therapy is often implemented by using a positive airway pressure device to deliver a pressurized stream of air through a conduit to a patient through a patient interface or mask positioned on the face of the patient. A gases humidifier may be used to humidify gases being delivered to the patient.

BRIEF SUMMARY

Patient interfaces that form one or more seals with the nares, nose and/or mouth of the patient are generally used when administering PAP therapy for the treatment of OSA. When selecting a patient interface for a particular patient, it is important to consider a number of factors, including the patient's comfortability with the patient interface and the patient's manner of breathing. Generally, a nasal mask adapted to only seal around the nose of the patient is perceived as less obstructive and more patient-friendly than a full-face mask adapted to seal around both the nose and mouth of the patient. However, patients who regularly breathe through the mouth or otherwise open the mouth during a PAP therapy session generally require a full-face mask to maximize the efficacy and comfort of the therapy. If a nasal mask is used with such patients, high gas flows passing through the mouth on exhalation can potentially dry out the oral mucosa, potentially causing discomfort to the patient. Additionally, gas leaks through the mouth can reduce the efficacy of the PAP therapy administered. Although care is generally taken to determine the patient's manner of breathing upon prescription of a patient interface, in some cases the patient's manner of breathing can change. For example, a patient using a nasal mask may be compelled to exhale through the mouth if experiencing nasal congestion (for example, due to allergies or illness). It is desired to determine the presence of a mouth puff event (periods of exhalation where the mouth happens to open) when a patient is wearing a nasal mask or other nasal interface.

Mouth puff, also known as valve-like mouth leak, can be characterized by regions of flatness in expiratory portions of flow waveforms corresponding to patient respiratory activity when the patient is wearing a nasal interface. Additionally, by studying the linear regression slope of expiratory portions of the flow waveform, the degree of flatness can be determined. However, it has been realized that if the entire expiratory window of a given breath in the flow waveform is used to determine the slope, steep transitions between inhalation and exhalation (or vice versa, steep transitions between exhalation and inhalation) can be present, potentially skewing the value of the slope and reducing the certainty of a mouth puff determination.

To account for steep transitions, the linear regression slope can be calculated using a sub-window of the expiratory window of a given breath in the flow waveform. The sub-window can be defined by a predetermined section of the expiratory window. For example, if the expiratory window extends from a first time $t_1$ to a second time $t_2$, the sub-window can extend from a third time $t_3$ that is at 20% or about 20% of the time between the first time $t_1$ and the second time $t_2$ and a fourth time $t_4$ that is at 80% or about 80% of the time between the first time $t_1$ and the second time $t_2$.

As another alternative, the sub-window might not be defined by a predetermined section of the expiratory window. The boundaries of the sub-window might be selected dynamically by analyzing characteristics of the expiratory window. In some cases, the boundaries of the sub-window might be selected by determining the first derivative of the expiratory window with respect to time (e.g. df/dt, where f represents a flow rate) and finding zero-crossings of the first derivative (e.g. regions where df/dt is zero or about zero). For example, the beginning of the sub-window might be selected such that is contemporaneous or about contemporaneous with the first zero-crossing of the first derivative of the expiratory window. In other configurations, the beginning of the sub-window might be selected such that it is contemporaneous or about contemporaneous with the second zero-crossing of the first derivative of the expiratory window. The end of the sub-window might be selected such that it is contemporaneous or about contemporaneous with the last zero-crossing of the first derivative of the expiratory window. Dynamically selecting the boundaries of the sub-window can improve the accuracy of the determination of a mouth puff event by accounting for idiosyncrasies of expiratory windows of individual breaths in a flow waveform.

In one aspect, this disclosure relates to a respiratory event determination system comprising a controller configured to determine a presence of a respiratory event as a function of a sub-window of an expiratory window of a breath, wherein the expiratory window extends between a first time $t_1$ and a second time $t_2$, and wherein the sub-window is limited to a portion of the expiratory window extending between a third time $t_3$ and a fourth time $t_4$, the third time $t_3$ being after the first time $t_1$ and/or the fourth time $t_4$ being before the second time $t_2$.

The third time $t_3$ may be is after the first time $t_1$ and the fourth time $t_4$ may be before the second time $t_2$.

The third time $t_3$ may lie in the range of about 5% to about 35% of the time between the first time $t_1$ and the second time $t_2$.

The third time $t_3$ may be at about 20% of the time between the first time $t_1$ and the second time $t_2$.

The fourth time $t_4$ may lie in the range of about 65% to about 95% of the time between the first time $t_1$ and the second time $t_2$.

The fourth time $t_4$ may be at about 80% of the time between the first time $t_1$ and the second time $t_2$.

The third time $t_3$ may be selected such that it is a function of a characteristic of the breath.

The third time $t_3$ may be selected such that it is a function of a zero-crossing of a derivative of the expiratory window.

The third time $t_3$ may be selected such that it is contemporaneous or about contemporaneous with a zero-crossing of a derivative of the expiratory window.

The derivative of the expiratory window may be the first derivative of the expiratory window.

The zero-crossing may be a first zero-crossing.

The zero-crossing may be a second zero-crossing.

The function may be a piecewise function.

The piecewise function may be such that the third time $t_3$ is selected such that it is set to a fifth time $t_5$ that is contemporaneous or about contemporaneous with a time $t_{zc1}$ of a first or second zero-crossing of a first derivative of the expiratory window if the time $t_{zc1}$ of the first or second zero-crossing is less than or equal to a first threshold time $t_{th1}$ between the first time $t_1$ and the second time $t_2$, and such that it is set to a sixth time $t_6$ if the time $t_{zc1}$ of the first or second zero-crossing is greater than the first threshold time $t_{th1}$ between the first time $t_1$ and the second time $t_2$.

The piecewise function may be such that the third time $t_3$ is selected such that it is set to a fifth time $t_5$ that is contemporaneous or about contemporaneous with a time $t_{zc1}$ of a first or second zero-crossing of a first derivative of the expiratory window if the time $t_{zc1}$ of the first or second zero-crossing is less than a first threshold time $t_{th1}$ between the first time $t_1$ and the second time $t_2$, and such that it is set to a sixth time $t_6$ if the time $t_{zc1}$ of the first or second zero-crossing is greater than or equal to the first threshold time $t_{th1}$ between the first time $t_1$ and the second time $t_2$ The sixth time $t_6$ may be earlier than the first threshold time $t_{th1}$.

The sixth time $t_6$ may lie in the range of about 5% to about 35% of the time between the first time $t_1$ and the second time $t_2$.

The sixth time $t_6$ may be at about 20% of the time between the first time $t_1$ and the second time $t_2$.

The first threshold time $t_{th1}$ may be a predetermined time between the first time $t_1$ and the second time $t_2$.

The fourth time $t_4$ may be selected as a function of a characteristic of the breath.

The fourth time $t_4$ may be selected such that it is a function of a zero-crossing of a derivative of the expiratory window.

The fourth time $t_4$ may be selected such that it is contemporaneous or about contemporaneous with a zero-crossing of a derivative of the expiratory window.

The derivative may be a first derivative of the expiratory window.

The zero-crossing may be a last zero-crossing.

The function may be a piecewise function.

The piecewise function may be such that the fourth time $t_4$ is selected such that it is set to a seventh time $t_7$ that is contemporaneous or about contemporaneous with a time $t_{zc2}$ of a last zero-crossing of the first derivative of the expiratory window if the time $t_{zc2}$ of the last zero-crossing is greater than or equal to a second threshold time $t_{th2}$ between the first time $t_1$ and the second time $t_2$, and such that it is set to an eighth time $t_8$ if the time $t_{zc2}$ of the first or second zero-crossing is less than the second threshold time $t_{th2}$ between the first time $t_1$ and the second time $t_2$.

The piecewise function may be such that the fourth time $t_4$ is selected such that it is set to a seventh time $t_7$ that is contemporaneous or about contemporaneous with a time $t_{zc2}$ of a last zero-crossing of the first derivative of the expiratory window if the time $t_{zc2}$ of the last zero-crossing is greater than a second threshold time $t_{th2}$ between the first time $t_1$ and the second time $t_2$, and such that it is set to an eighth time $t_8$ if the time $t_{zc2}$ of the first or second zero-crossing is less than or equal to the second threshold time $t_{th2}$ between the first time $t_1$ and the second time $t_2$ The eighth time $t_8$ may be greater than the second threshold time $t_{th2}$.

The eighth time $t_8$ may lie in the range of about 65% to about 95% of the time between the first time $t_1$ and the second time $t_2$.

The eighth time $t_8$ may be at about 80% of the time between the first time $t_1$ and the second time $t_2$.

The second threshold time $t_{th2}$ may be a predetermined time between the first time $t_1$ and the second time $t_2$.

The respiratory event may comprise a mouth puff event.

The controller may be further configured to generate a non-event determination signal if a linear regression slope of the expiratory window between the third time $t_3$ and the fourth time $t_4$ is greater than a respiratory event slope threshold $res_t$.

The controller may be further configured to generate an event determination signal if a linear regression slope of the expiratory window between the third time $t_3$ and the fourth time $t_4$ is less than or equal to a respiratory event slope threshold $res_t$.

The controller may be further configured to generate a determination signal ds upon determination of the presence of a respiratory event, and generate an event epoch signal if the determination signal is present for at least a first time period $tp_1$ within a second time period $tp_2$.

The controller may be further configured to generate a determination signal ds upon determination of the presence of a respiratory event, and generate an event epoch signal if the determination signal is present for at least a first number of breaths $tb_1$ within a second number of breaths $tb_2$.

In a second aspect, this disclosure relates to a respiratory event determination system comprising a controller configured to determine a presence of a respiratory event as a function of a sub-window of an expiratory window of a breath, wherein the expiratory window extends between a first time $t_1$ and a second time $t_2$, and wherein the sub-window is limited to a portion of the expiratory window extending between a third time $t_3$ and a fourth time $t_4$, and wherein the third time $t_3$ is a function of a time of a first or second zero-crossing of a first derivative of the expiratory window.

The third time $t_3$ may be contemporaneous or about contemporaneous with the first or second zero-crossing of the first derivative of the expiratory window.

The fourth time $t_4$ may be a function of a time of a last zero-crossing of a first derivative of the expiratory window.

The fourth time $t_4$ may be contemporaneous or about contemporaneous with the last zero-crossing of the first derivative of the expiratory window.

In a third aspect, this disclosure relates to a respiratory event determination system comprising a controller configured to determine a presence of a respiratory event as a function of a sub-window of an expiratory window of a breath, wherein the expiratory window extends between a first time $t_1$ and a second time $t_2$, and wherein the sub-window is limited to a portion of the expiratory window extending between a third time $t_3$ and a fourth time $t_4$, and wherein the fourth time $t_4$ is a function of a time of a last zero-crossing of a first derivative of the expiratory window.

The fourth time $t_4$ may be contemporaneous or about contemporaneous with the last zero-crossing of the first derivative of the expiratory window.

In a fourth aspect, this disclosure relates to a method of using the respiratory event determination system according to any one of the above statements to determine the presence of a respiratory event.

The respiratory event may be a mouth puff event.

In a fifth aspect, this disclosure relates to a respiratory therapy system comprising a respiratory event determination system according to any one of the above statements relating to the respiratory event determination system.

The respiratory therapy system may comprise a flow generator.

The flow generator may be a PAP apparatus.

The controller may be further configured to adjust a pressure and/or flow rate of gases generated by the flow generator as a function of the determined presence or non-presence of the respiratory event.

The respiratory event may be a mouth puff event.

The pressure and/or flow rate of gases generated by the flow generator may be decreased upon determination of the mouth puff event.

The respiratory therapy system may further comprises a humidifier.

The controller may be further configured to adjust an output humidity of the humidifier as a function of the determined presence or non-presence of the respiratory event.

The respiratory event may be a mouth puff event.

The output humidity of the humidifier may be increased upon determination of the mouth puff event.

The respiratory therapy system may further comprise a sealing patient interface.

The respiratory therapy system may further comprise a gas delivery conduit that links the flow generator to the sealing patient interface.

BRIEF DESCRIPTION OF THE DRAWINGS

Specific embodiments and modifications thereof will become apparent to those skilled in the art from the detailed description herein having reference to the figures that follow, of which.

DETAILED DESCRIPTION

Figure 1:
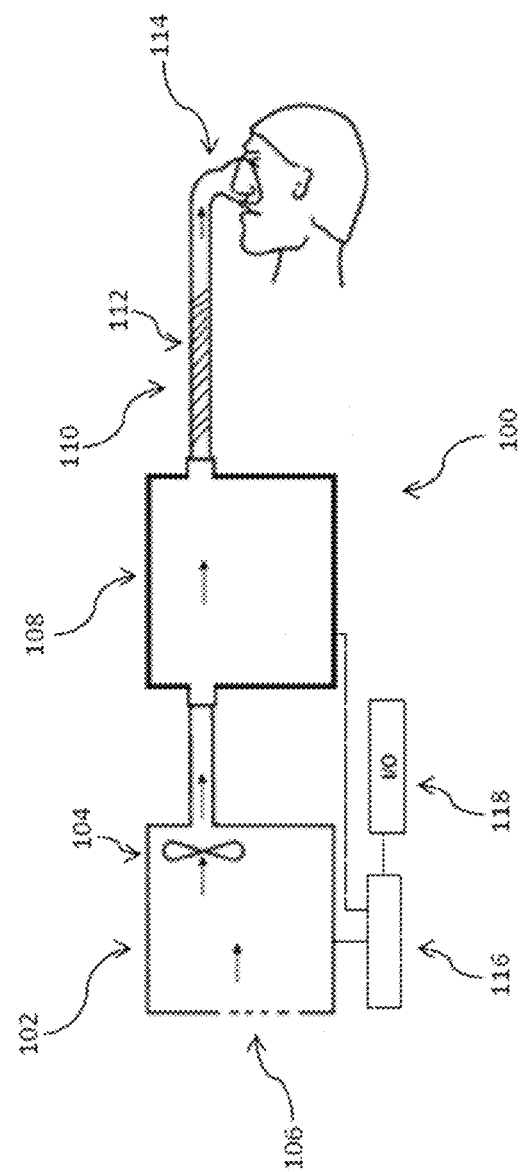
FIG. 1 shows a schematic diagram of a respiratory therapy system.

With reference to the non-limiting exemplary embodiment illustrated in FIG. 1, a schematic of a respiratory therapy system 100 is shown. The respiratory therapy system 100 comprises a flow generator 102. The flow generator 102 comprises a PAP device. The PAP device comprises a blower 104. The flow generator 102 receives gases from a gases inlet 106. Gases received by the flow generator 102 are propelled towards a patient. In the illustrated configuration, the flow generator 102 transfers the received gases to a gases humidifier 108. The gases humidifier 108 humidifies the gases. The gases humidifier 108 may also heat the gases. In the illustrated configuration, the gases humidifier 108 is a pass-over humidifier. Humidified gases are passed from a humidifier outlet to a gases conduit 110. The gases conduit 110 comprises a heater 112. The heater 112 heats gases passing through the gases conduit 110. The heater 112 reduces or prevents the condensation of moisture along the walls of the gases conduit 110. Gases are passed from the gases conduit 110 to a patient interface 114 through which they are delivered to a user. The respiratory therapy system 100 comprises a controller 116 (including electronic components such as a microprocessor, for example but without limitation) that controls the operation of the flow generator 102. The controller 116 also controls the operation of the gases humidifier 108. The respiratory therapy system 100 comprises an input/output (I/O) module 118. The I/O module 118 comprises a way for a user to interact with and set parameters for the flow generator 102 and/or gases humidifier 108 (e.g. through the controller 116) as well as receive information regarding the operation of the respiratory therapy system 100 and/or its components or peripherals or accessories. The I/O module 118 may comprise, for example, buttons, knobs, dials, switches, levers, touch screens, speakers, displays and/or other input or output elements. In some configurations, the I/O module 118 may be adapted to communicate with the controller 116 via a physical data connection (e.g. via a wire, etc). In other configurations, the I/O module 118 may be adapted to communicate with the controller 116 via a wireless data connection (e.g. via Bluetooth, WiFi, etc). In other configurations, the gas conduit 110 may not have a heater 112. In other configurations, the gases humidifier 108 may not be present, and the flow generator 102 may interface with the patient interface 114 (e.g. either directly or via the gases conduit 110). In other configurations, the I/O module 118 may not be present. In some such configurations, in lieu of an input device the flow generator 102 may be controlled dependent on the determination of a patient usage signal (e.g. via sensing of respiratory activity through the use of a flow or pressure sensor, sensing of exhaled carbon dioxide using a $CO_2$ sensor, etc). In some configurations the flow generator 102 comprises a motorized blower or compressor.

The flow generator 102 and gases humidifier 108 may be part of an integrated flow delivery system or may share a housing. In the illustrated configuration, the flow generator 102 is a PAP apparatus. In other configurations, the flow generator 102 may comprise components other than PAP apparatus, including but not limited to high flow therapy devices or ventilation devices. If a PAP apparatus is utilized, the PAP apparatus may comprise a number of PAP apparatus variants, including but not limited to continuous positive airway pressure (CPAP) apparatus, automatically adjusting positive airway pressure (APAP or AutoPAP) apparatus or bi-level positive airway pressure (BiPAP or bi-level PAP) apparatus. The patient interface 114 comprises a mask adapted to seal about and channel gases to the nose of the user. In other configurations, the patient interface 114 may comprise a semi-sealing or non-sealing interface to provide a flow of gases to the nose of the user (a nasal interface). In other configurations the patient interface 114 may comprise a nasal pillows mask, a nasal cannula, combinations of the above, or other gas conveying elements, apparatus or systems.

Figure 2:
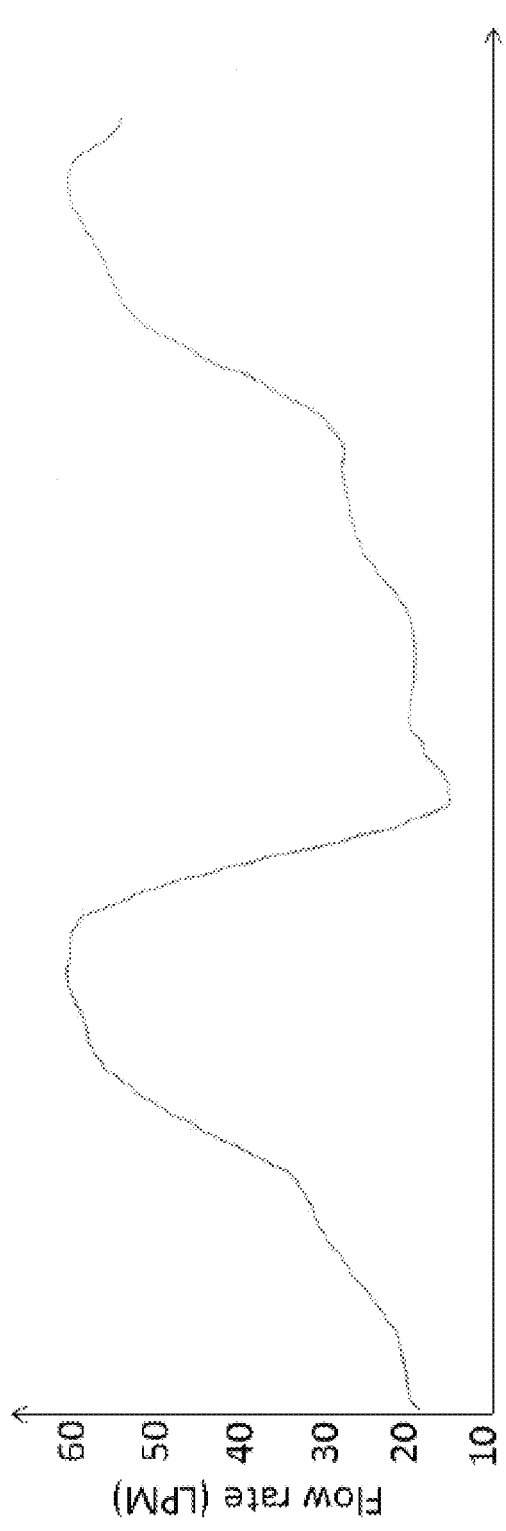
FIG. 2 shows a flow waveform of an exemplary normal breath sample.

FIG. 2 shows an exemplary flow rate versus time graph. The graph shows a flow waveform representative of a normal breathing pattern as measured using a flow sensor in a PAP apparatus that is delivering CPAP therapy. As shown, the flow waveform is approximately sinusoidal or has a substantially regular crescendo-decrescendo pattern. The flow waveform is marked by periods of exhalation (in which the recorded flow rate falls as low as about 15 liters per minute (LPM) under the positive pressure gas flow) and by periods of inhalation (in which the recorded flow rate increases as high as about 60 LPM under the positive pressure gas flow).

Figure 3:
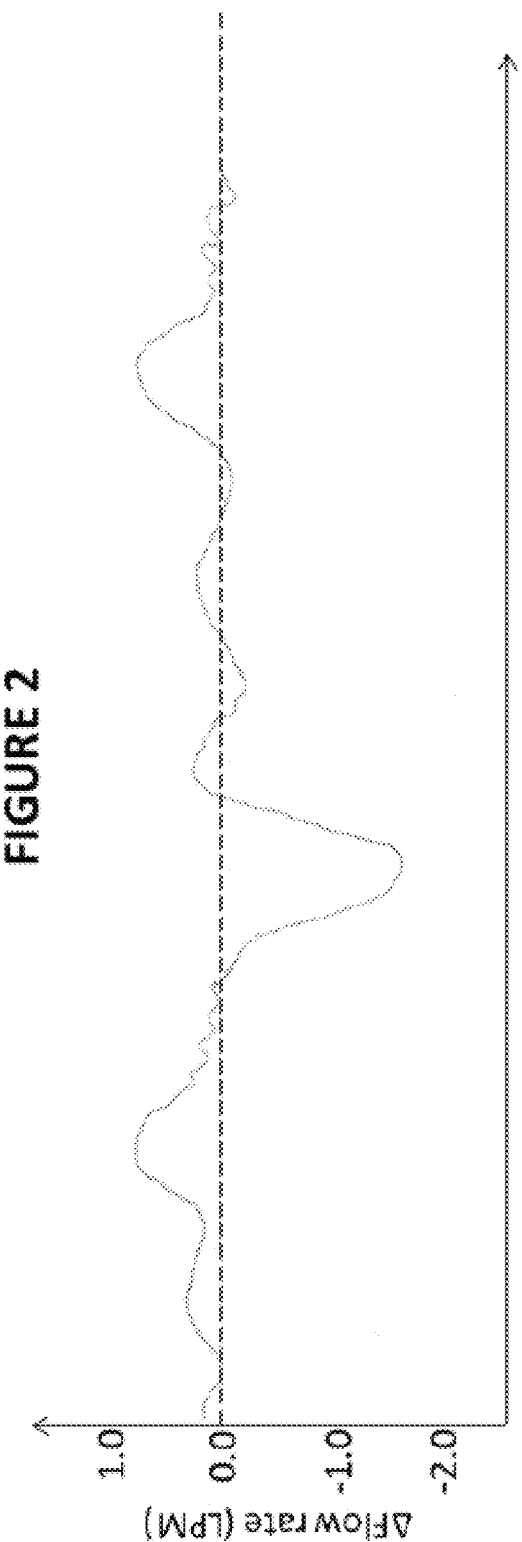
FIG. 3 shows the first derivative of the flow waveform of FIG. 2 with respect to FIG. 4 shows a flow waveform of an exemplary breath sample displaying signs of mouth puff.

FIG. 3 shows the first derivative of the flow rate versus time graph shown in FIG. 2 with respect to time (first derivative of the flow waveform). As shown, the flow waveform (FIG. 2) and the first derivative of the flow waveform (FIG. 3) are presented along the same time scale T. The first derivative of the flow waveform comprises some normal oscillation around the zero-crossing line (horizontal dotted line pertaining to df/dt=0) during periods of exhalation. No particular irregularities are shown.

Figure 4:
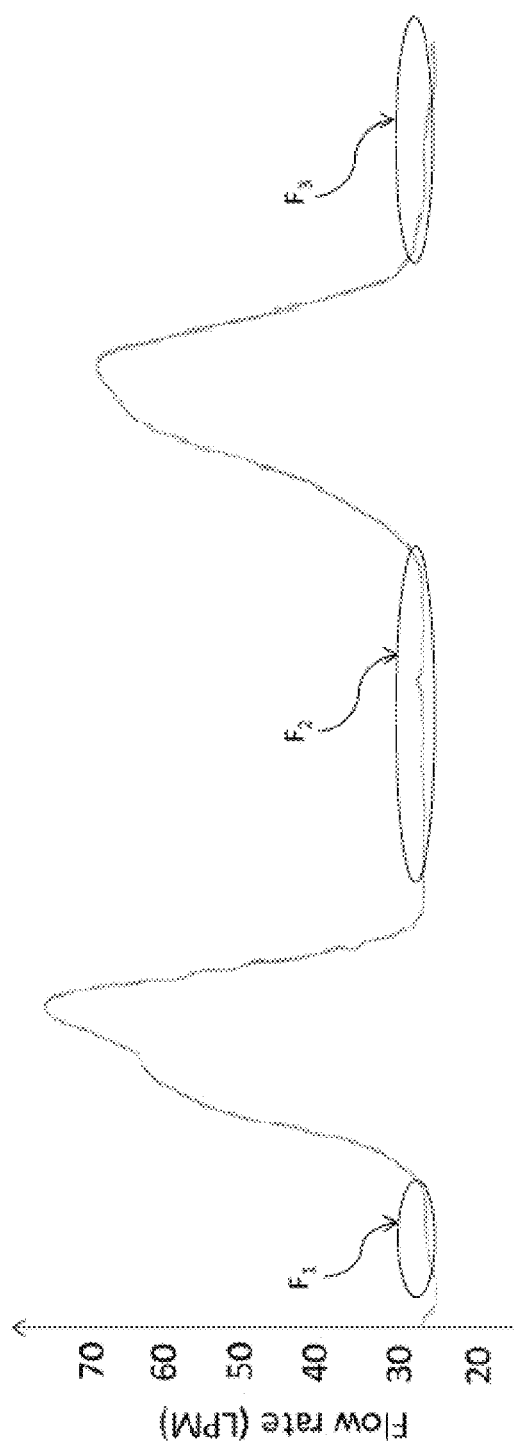

FIG. 4 shows another exemplary flow rate versus time graph. The graph shows a flow waveform representative of an irregular breathing pattern as measured using a flow sensor in a PAP apparatus that is delivering CPAP therapy to a patient wearing a nasal mask or a nasal pillow mask or other nasal interface. The illustrated flow waveform exhibits signs of mouth puff. As shown, the flow waveform is not as sinusoidal as the flow waveform representative of normal breathing shown in FIG. 2. The illustrated flow waveform is characterized by periods of exhalation (in which the recorded flow rate falls as low as about 25 LPM under the positive pressure gas flow) and by periods of inhalation (in which the recorded flow rate increases as high as about 75 LPM under the positive pressure gas flow). However, the periods of exhalation are shown to have portions $F_1$, $F_2$, $F_3$ that are substantially flat relative to the flow waveform representative of normal breathing shown in FIG. 2. The portions $F_1$, $F_2$, $F_3$ are substantially flat because much of the exhaled flow escapes through the mouth rather than through the nose.

Figure 5:
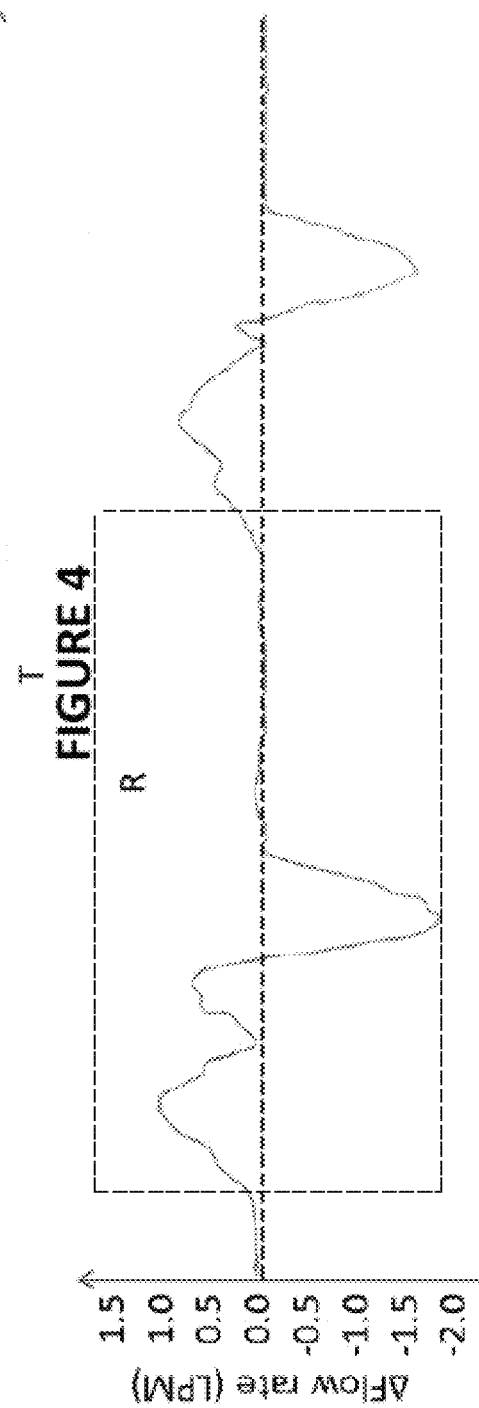
FIG. 5 shows the first derivative of the flow waveform of FIG. 4 with respect to time.

FIG. 5 shows the first derivative of the flow rate versus time graph shown in FIG. 4 with respect to time (first derivative of the flow waveform). As shown, the flow waveform (FIG. 4) and the first derivative of the flow waveform (FIG. 5) are presented along the same time scale T. The first derivative of the flow waveform comprises oscillations around the 'zero-crossing' line (horizontal dotted line pertaining to df/dt=0) during periods of exhalation that are relatively smaller than the oscillations seen in the flow waveform presented in FIG. 3. The small oscillations give the impression that the flow waveform around these periods of exhalation is substantially flat.

Figure 6:
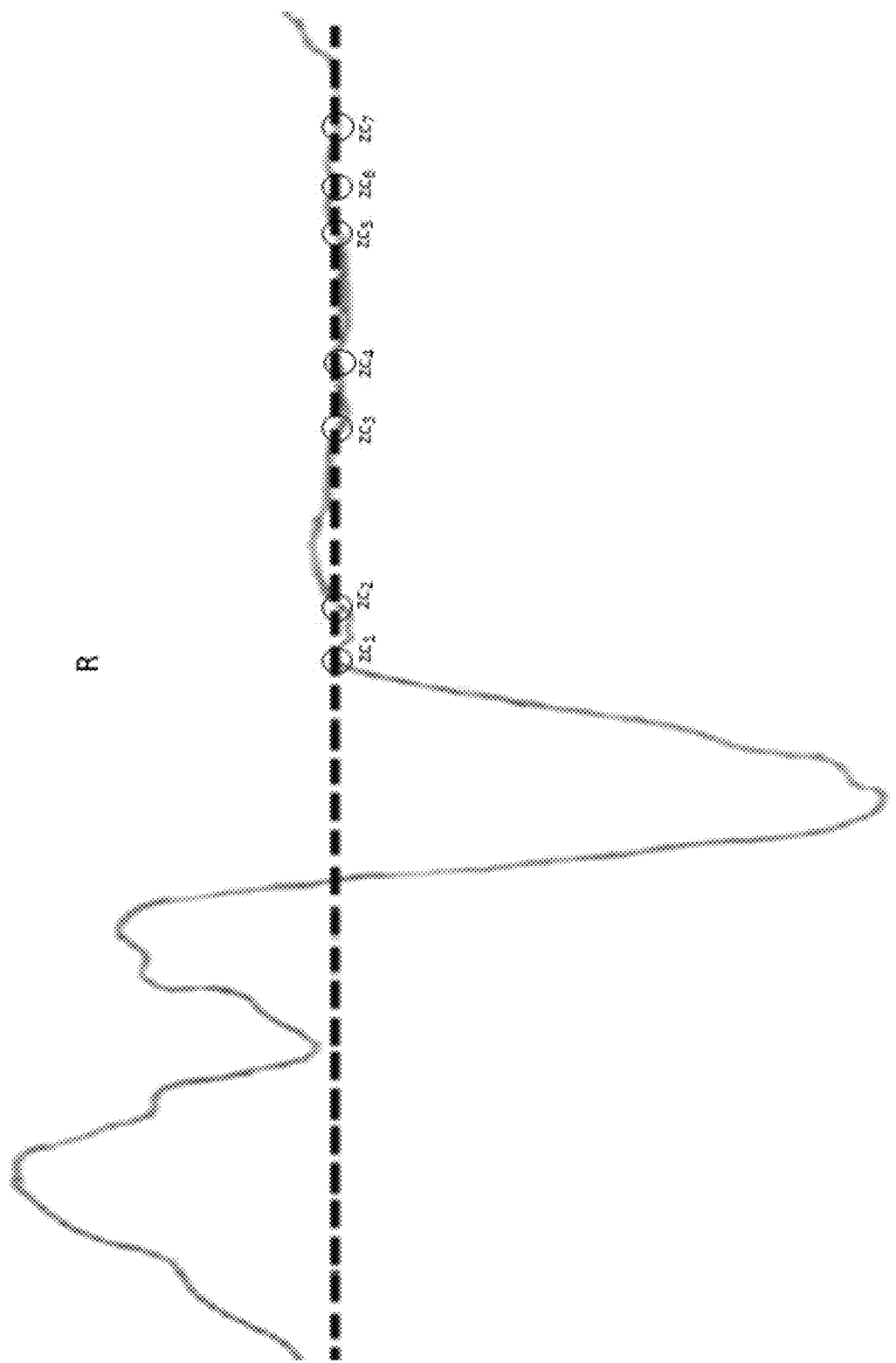
FIG. 6 shows a magnified region of the first derivative shown in FIG. 5.

FIG. 6 shows a magnified portion R of the first derivative of the flow waveform illustrated in FIG. 5. The magnified portion R corresponds with the first inhalation and first full exhalation (characterized by substantially flat portion $F_2$) shown in the flow waveform of FIG. 5. As described, the first derivative of the flow waveform illustrated in FIGS. 5 and 6 shows small oscillations around the zero-crossing line. The first derivative of the flow waveform crosses the zero-crossing line at a number of points $zc_1$, $zc_2$, $zc_3$, $zc_4$, $zc_5$, $zc_6$, $zc_7$ (e.g. zero-crossing points or zero-crossings) as it oscillates to positions above and below the zero-crossing line over time. In some cases, and as described elsewhere in the disclosure with reference to the accompanying figures, these zero-crossings can be used to select portions of the expiratory window of the flow waveform for the determination of the mouth puff events.

It should be understood that although the remaining portion of the disclosure is directed towards the use of portions of the expiratory window of flow waveforms for determining the presence of mouth puff, certain features, aspects and advantages of at least one of the embodiments disclosed herein, including but not limited to embodiments pertaining to the selection of portions of the expiratory window, could be applied for determining the presence and/or type and/or severity of other respiratory events or conditions. As an example, portions of the expiratory window might be useful for determining the presence of a general mouth leak rather than mouth puff per se. For a mouth puff (valve-like mouth leak), the mouth opens during expiration only, or for part of expiration only. In contrast, for mouth leak the mouth may be open during both inspiration and expiration. As another example, instabilities in select portions of the expiratory window of a given patient might in some cases indicate that the patient's lungs are damaged or dysfunctional, or that the patient is congested, wheezy or otherwise ill. The degree or severity of the instabilities might indicate the degree or severity of lung damage, lung dysfunction, congestion, or illness. As another example, determined irregularities in select portions of the expiratory flow waveform of a given patient might be used to assist in distinguishing between obstructive sleep apnea and central sleep apnea. However, if the whole expiratory window were used in some such cases, aberrations at, for example, the beginning or end of the window might skew the analysis of the expiratory window, in turn causing the generation of an incorrect conclusory output signal.

For ease of description, the steps of various methods disclosed herein, including but not limited to the methods 200, 300, 400 described with reference to the accompanying figures, will be described as being performed by the controller 116 described elsewhere in this disclosure with reference to FIG. 1. However, it should be understood that the methods 200, 300, 400 might be performed by other elements, apparatus or systems, or might be performed in other ways. For example, multiple controllers might be used to perform different parts of the methods 200, 300, 400. As another example, a controller outside of the respiratory therapy system 100 but associated with the respiratory therapy system 100 (for example, a controller of a server in electronic communication with the respiratory therapy system) might be used to perform at least parts of the methods 200, 300, 400. Additionally, it should be understood that certain features, aspects and advantages of the present disclosure might be obtained by performing only portions of the methods 200, 300, 400 described (e.g. sub-methods). In some configurations, certain portions of the methods 200, 300, 400 may be eschewed while retaining certain features, aspects and advantages of the present disclosure. Additionally, it should be understood that certain features, aspects and advantages of the present disclosure might be obtained by performing steps of the methods 200, 300, 400 in a different order to that shown and described with reference to the accompanying figures.

Figure 7:
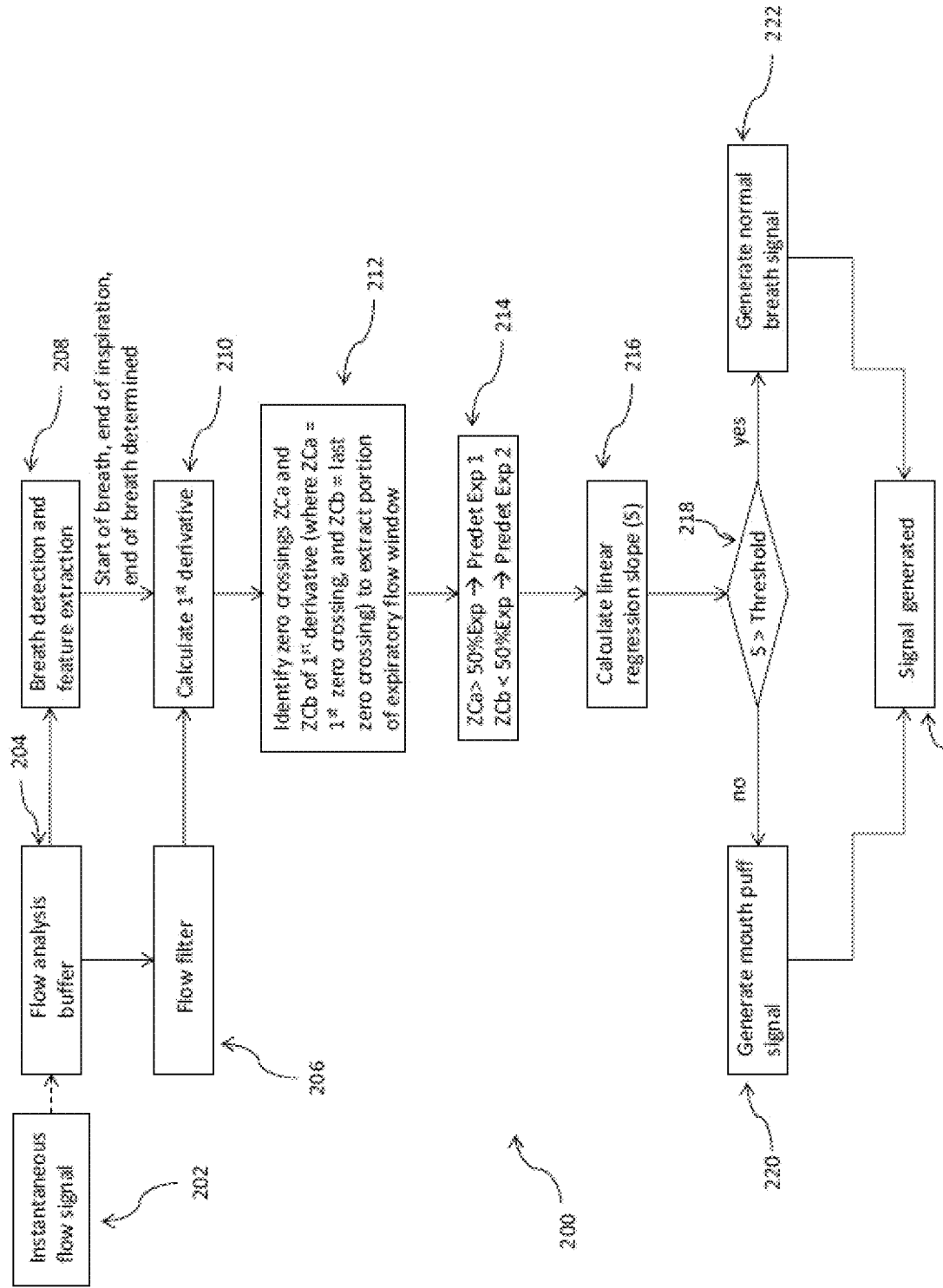
FIG. 7 shows a flow chart demonstrating a non-limiting exemplary method of determining a mouth puff event.

FIG. 7 illustrates a flow chart describing a non-limiting exemplary method 200 for determining the presence of mouth puff. The method 200 comprises a number of steps. In step 202, an instantaneous flow signal is obtained. The instantaneous flow signal might be obtained, for example, by a flow sensor positioned in a portion of the respiratory therapy system 100 exposed to gas flow and in pneumatic communication with an airway of a patient. The instantaneous flow signal pertains to an instantaneous flow value.

In step 204, the instantaneous flow signal is added to a flow analysis buffer. The flow analysis buffer is configured to store a number of instantaneous flow readings for analysis in step 208, which is described later in this disclosure.

In step 206, the instantaneous flow signal is passed to a flow filter. The flow filter comprises a buffer configured to store a buffer of flow signals. The flow filter is also configured to modulate the flow signals stored in order to improve the signal-to-noise ratio of the signals. To improve the signal-to-noise ratio, the flow filter applies a digital filter to the flow signals in order to smooth the signals. The digital filter can comprise any one of a number of digital filters adapted to smooth signals, including but not limited to a Savitsky-Golay filter.

In step 208, and in parallel with or at or about the same time as step 206, the controller 116 is configured to analyze the flow signals recorded in the flow analysis buffer in step 204 to determine the presence an individual breath in the buffer. The presence of individual breaths (an individual breath comprising inspiration and expiration) may be noted by analyzing the signals in the flow analysis buffer to identify signals or points within the flow analysis buffer related to breath features, including but not limited to virtual peaks, troughs, slopes and flat regions. Using these points, the controller 116 may then determine the presence of breath features including but not limited to the start of a given breath, the end of the given breath, the start of inspiration in the given breath, the end of inspiration in the given breath, pauses between inspiration and expiration, the start of expiration in the given breath, the end of expiration in the given breath, and pauses between expiration and inspiration. In the illustrated non-limiting configuration, the start of a given breath, the end of inspiration of the given breath, and the end of the given breath are determined using the flow analysis buffer. In some configurations, the controller 116 may perform a process of interpolation to construct a virtual flow waveform using the flow signals and analyze components of the virtual flow waveform to identify individual breaths and breath features.

As each breath is determined, pointers relating to the positions of breath features of the determined breath are used in step 210 together with relevant portions of the flow signals within the smoothed flow buffer obtained in step 206. In step 210, a first derivative of the flow signals within the smoothed flow buffer with respect to time is generated (df/dt).

In an alternative configuration, steps 206 and 208 need not necessarily occur in parallel or at or about the same time. In some configurations, steps 206 and 208 might occur in series. Flow signals received in the flow analysis buffer during step 204 may be smoothed using the flow filter in step 206, and a distinct breath and associated breath features may be found in step 208 by directly analyzing the smoothed flow signals obtained using the flow buffer. This directly analyzed set of smoothed flow signals may instead be used in step 210.

The expiratory window of a breath is a part of the breath over which expiration occurs. As described elsewhere in this disclosure, analyzing portions of the expiratory window of a breath can be useful for determining the presence of respiratory events including but not limited to mouth puff events. However, in some cases if the entire expiratory window is analyzed, steep transitions at the beginning or end of the expiratory window (due to, for example, the presence of an exhalation that is only initially particularly forceful or the presence of an exhalation with an unusually abrupt end) can skew the analysis of the expiratory window for signs of respiratory events. Additionally, the nature of a particular patient's physiology, illness, or manner of breathing can cause aberrations to be detected at the beginning and end of the expiratory window, which in some cases can cause an incorrect determination of the presence or absence of a particular respiratory event.

Accordingly, for an expiratory window extending between a first time $t_1$ and second time $t_2$, it has been realized that a sub-window within the expiratory window can be selected and analyzed for the presence of mouth puff. The sub-window may be defined as extending between a third time $t_3$ and a fourth time $t_4$, wherein the third time $t_3$ is later than the first time $t_1$, and wherein the fourth time $t_4$ is contemporaneous, about contemporaneous, or earlier than the second time $t_2$. Alternatively, sub-window may be defined as extending between a third time $t_3$ and a fourth time $t_4$, wherein the third time $t_3$ is contemporaneous, about contemporaneous or later than the first time $t_1$, and wherein the fourth time $t_4$ is earlier than the second time $t_2$.

In some configurations, a sub-window within the expiratory window can be selected by finding zero-crossings (e.g. points where df/dt=0) of the first derivative of the flow waveform represented by the smoothed flow signals. By selecting the sub-window using the zero-crossings, the sub-window can be selected on a breath-by-breath basis, allowing for the method 200 to be used effectively on a diverse collection of patients having differently shaped expiratory windows.

In step 212, zero-crossings of the first derivative of the expiratory window of the flow waveform are identified by determining if the value of df/dt of a given portion of the first derivative of the expiratory window is 0 or about 0 (for example, if the value of df/dt is less than or equal to 0+a predetermined value, or if the value of df/dt is greater than or equal to 0—a predetermined value). As described elsewhere in this specification, FIG. 6 shows zero-crossings $zc_1$-$zc_7$ of a first derivative of an expiratory window of a flow waveform. Once the zero-crossings are identified, the sub-window of the expiratory window may be selected such that the third time $t_3$ is contemporaneous or about contemporaneous with the time at which the first zero-crossing $zc_a$ was observed and such that the fourth time $t_4$ is contemporaneous or about contemporaneous with the time at which the last zero-crossing $zc_b$ was observed. 'About contemporaneous,' as used here, could mean 'close to' the time at which the relevant zero-crossing $zc_a$, $zc_b$ was observed (for example but without limitation, within 100, within 90, within 80, within 70, within 60, within 50, within 40, within 30, within 20, or within 10 milliseconds of the time at which the relevant zero-crossing $zc_a$, $zc_b$ was observed. As a non-limiting example, and with reference to FIG. 6, the first zero-crossing $zc_1$ and the last zero-crossing $zc_7$ could be chosen to define $t_3$ and $t_4$ of the sub-window.

It should be understood that although in the non-limiting example, the first and last zero-crossings were used to define the sub-window, in other configurations other zero-crossings might be used. For example, and with reference to FIG. 6, in some configurations the second zero-crossing $zc_2$ might be chosen to define $t_3$. In some configurations, the second-to-last zero-crossing $zc_6$ might be chosen to define $t_4$.

With further reference to the non-limiting example described with reference to FIG. 7, in step 214 the first zero-crossing $zc_a$ and the last zero-crossing $zc_b$ are checked with reference to their positions within the expiratory window. In some cases, the flow waveform analyzed may be such that the first zero-crossing $zc_a$ of the first derivative of the expiratory portion of the flow waveform happens very late in the expiratory portion of the breath represented by the flow waveform. In some cases, the flow waveform analyzed may be such that the last zero-crossing $zc_b$ of the first derivative of the expiratory portion of the flow waveform happens very early in the expiratory portion of the breath represented by the flow waveform. If the first zero-crossing $zc_a$ occurs too late, or if the last zero-crossing $zc_b$ occurs too early, the sub-window defined using the zero-crossings $zc_a$, $zc_b$ may be too small for analysis. The sub-window may not accurately or thoroughly represent the best portion of the expiratory window for analysis.

In step 214, then, if the first zero-crossing $zc_a$ of the first derivative occurs at a time that is later than a first predetermined time or threshold time $t_{th1}$ within the expiratory window, instead of being set such that it is contemporaneous or about contemporaneous with the time of the first zero-crossing $zc_a$, the third time $t_3$ of the sub-window may be set such that it is contemporaneous or about contemporaneous with a second predetermined time or threshold time $t_{th2}$. If the last zero-crossing $zc_b$ of the first derivative occurs at a time that is earlier than a third predetermined time or threshold time $t_{th3}$, instead of being set such that it is contemporaneous or about contemporaneous with the time of the last zero-crossing $zc_b$, the fourth time $t_4$ of the sub-window may be set such that it is contemporaneous or about contemporaneous with a fourth predetermined time or threshold time $t_{th4}$.

As an non-limiting example, and as shown in step 214, the first threshold time $t_{th1}$ is set to the 50% portion of the expiratory window (e.g. set to a time halfway through the expiratory window), the second threshold time $t_{th2}$ is set to the 20% portion of the expiratory window (e.g. set to a time 1/5 of the way through the expiratory window), the third threshold time $t_{th3}$ is set to the 50% portion of the expiratory window, and the fourth threshold time $t_{th4}$ is set to the 80% portion of the expiratory window. If the first zero-crossing $zc_a$ is determined to occur at the 60% portion of the expiratory window, and the last zero-crossing is determined to occur at the 90% portion of the expiratory window, then the sub-window is defined such that it extends between the third time $t_3$, which is set to the 20% portion of the expiratory window ($t_{th2}$), and the fourth time $t_4$, which is set to the 90% portion of the expiratory window ($t_{zcb}$). In some embodiments, the second threshold time $t_{th2}$ may be about 5% to 35% of the expiratory window. In some embodiments, fourth threshold time may be about 65% to about 95% of the expiratory window.

In light of step 214 as described, the third and fourth times $t_3$, $t_4$ may be considered piecewise functions of the times of the first and last zero-crossings of the first derivative:

$$t_3 = f(t_{zca}) = \begin{cases} t_{zca}, & \text{if } t_{zca} < t_{th1} \\ t_{th2}, & \text{if } t_{zca} \geq t_{th1} \end{cases}$$

$$t_4 = f(t_{zcb}) = \begin{cases} t_{zcb}, & \text{if } t_{zcb} > t_{th3} \\ t_{th4}, & \text{if } t_{zcb} \leq t_{th3} \end{cases}$$

where $t_{zca}$ is the determined time of the first 'zero-crossing' within the expiratory window and $t_{zcb}$ is the determined time of the last 'zero-crossing' within the expiratory window.

In step 216, once the third and fourth times $t_3$, $t_4$ of the sub-window of the expiratory window are defined, a linear regression slope S of the portion of the expiratory flow waveform represented by the sub-window is calculated between the third and fourth times $t_3$, $t_4$.

In step 218, the calculated linear regression slope S of the portion of the expiratory flow waveform is checked against a slope threshold $S_{th}$. If the calculated linear regression slope S is determined to be greater than the slope threshold $S_{th}$, the breath represented in part by the expiratory window is scored as a normal breath (step 222). If the calculated linear regression slope S is determined to be less than or equal to the slope threshold $S_{th}$, the breath represented in part by the expiratory window is scored as a mouth puff breath (step 220). As a non-limiting example, the slope threshold is 0.015 lpm2. After either of steps 220 or 222, the controller 116 generates a signal indicative of the type of breath that was scored (e.g. either a mouth puff breath as scored in step 220 or a normal breath as scored in step 222, dependent on the calculated linear regression slope comparison conducted in step 218).

It should be understood that although the above method 200 is described in terms of finding zero-crossings of the first derivative of the expiratory window, in other configurations other derivatives of the expiratory window might be analyzed. For example but without limitation, aspects of the second, third or fourth derivative of the expiratory window might be used to score a mouth puff breath.

Figure 8:
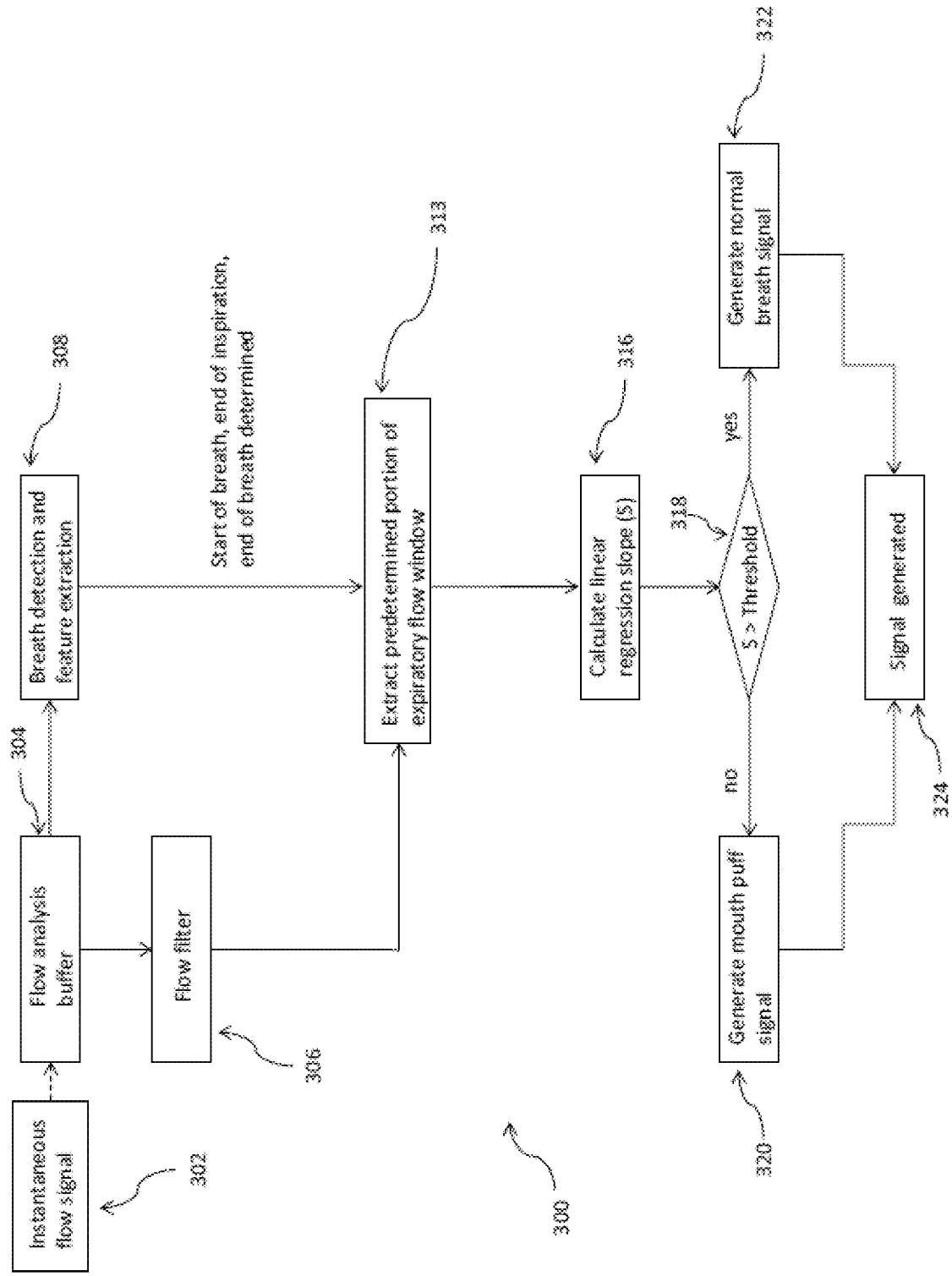
FIG. 8 shows a flow chart demonstrating a non-limiting alternative exemplary method of determining a mouth puff event.

FIG. 8 illustrates a flow chart describing an alternative non-limiting exemplary method 300 for determining the presence of mouth puff. In the method 300, many of the steps used are the same or similar to those described elsewhere in this disclosure with reference to FIG. 7. Similar reference numerals have been used to designate portions of the method 300. Instead of performing steps 210, 212, and 214 to determine zero-crossings of the first derivative of expiratory window and define the sub-window using the zero-crossings, step 313 may be performed. In step 313, predetermined times are used to select the third time $t_3$ and the fourth time $t_4$ of the sub-window of the expiratory window. The third time $t_3$ may be set to a first predetermined time $tp_1$ and the fourth time $t_4$ may be set to a second predetermined time $t_{p2}$. As a non-limiting example, if the first predetermined time $tp_1$ is set to the 20% portion of the expiratory window and the second predetermined time $t_{p2}$ is set to the 80% portion of the expiratory window, then in step 313 the sub-window may be defined by a third time $t_3$=20% and a fourth time $t_4$=80%. It should be understood that the sub-window might be limited in other manners. For example, the beginning of the sub-window might coincide with the beginning of the expiratory window (e.g. $t_3$=0% portion of the expiratory window) and only the end of the sub-window might be earlier than the end of the expiratory window (e.g. $t_4$<100% portion of the expiratory window). As another example, the beginning of the sub-window might be later than the beginning of the expiratory window (e.g. $t_3$>0% portion of the expiratory window) and the end of the sub-window might coincide with the end of the expiratory window (e.g. $t_4$=100% portion of the expiratory window). In some embodiments, the beginning of the sub window may be about 5% to 35% of the expiratory window. In some embodiments, the end of the sub-window may be about 65% to about 95% of the expiratory window. Although dynamically determining the third time $t_3$ and the fourth time $t_4$ of the sub-window as performed in steps 210, 212, 214 of the method 200 shown in FIG. 7 is preferred, limiting the sub-window as in method 300 can still improve the accuracy and/or precision of the determination of a mouth puff breath.

Figure 9:
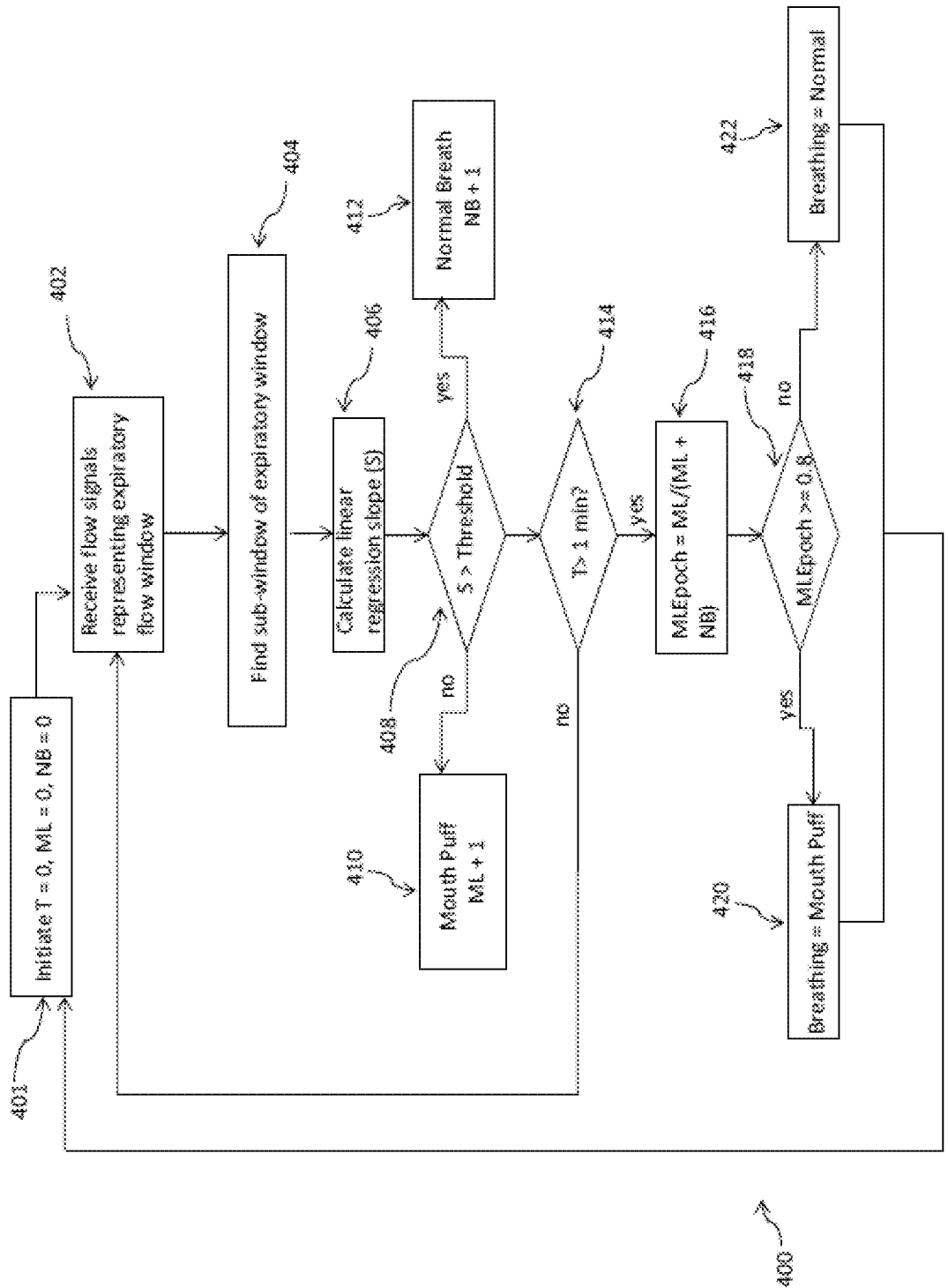
FIG. 9 shows a flow chart demonstrating a non-limiting exemplary method of determining a mouth puff epoch event.

FIG. 9 illustrates a flow chart describing a non-limiting exemplary method 400 for determining the presence of a mouth puff epoch. A mouth puff epoch is an event representing the presence of a considerable number or percentage of mouth puff breaths over the course of a predetermined time period. The determination of a mouth puff epoch can improve the certainty of a diagnosis of mouth puff for a patient by requiring that a substantial number or proportion of breaths in a given time period be classified as 'mouth puff' breaths before a determination can be made as shown in the disclosure below. In the illustrated configuration, the predetermined time period is 1 minute. However, in other configurations, other predetermined periods of time (including but not limited to 30 seconds, 1.5 minutes, 2 minutes, 5 minutes, or 10 minutes) might be used.

A time counter T representing the time elapsed since the start of the method 400 is initialized to zero in step 401 before moving on to step 402. Additionally, a mouth puff counter ML and a normal breathing counter NB are initialized to zero. The functions of the mouth puff counter ML and the normal breathing counter NB are described below.

In step 402, flow signals are received representing the expiratory window of a breath. The flow signals may be processed in a number of manners, including but not limited to manners that are the same as or similar to those described elsewhere in this disclosure with reference to steps 204, 206, and/or 208 and FIG. 7.

In step 404, a sub-window of the expiratory window of the breath is determined. The sub-window may be determined in a number of manners, including but not limited to manners that are the same as or similar to those described elsewhere in this disclosure with reference to steps 210, 212, 214 and FIG. 7 or to those described elsewhere in this disclosure with reference to step 313 and FIG. 8.

In step 406, a linear regression slope S of the sub-window is determined. The linear regression slope S of the sub-window may be determined in a number of manners, including but not limited to manners that are the same as or similar to those described elsewhere in this disclosure with reference to step 216 and FIG. 7.

In step 408, the determined linear regression slope S is compared against a threshold slope. The determined linear regression slope S may be compared in a number of manners, including but not limited to manners that are the same as or similar to those described elsewhere in this disclosure with reference to step 218 and FIG. 7.

Dependent of the output of the comparison in step 408, either a mouth puff is scored and the mouth puff counter ML is incremented by 1 (step 410) or normal breathing is scored and the normal breathing counter NB is incremented by 1 (step 412).

After incrementing either the mouth puff counter ML in step 410 or the normal breathing counter NB in step 412, the timer T is checked in step 414. If the timer T indicates that less than one minute has elapsed since initialization, the method 400 loops such that step 402 is performed on the next expiratory window received. If at least one minute has elapsed, step 416 is performed.

In step 416, an MLEpoch variable is calculated. In the illustrated example, MLEpoch equals (ML/(ML+NB)). As an example, if 9 mouth puff breaths (ML=9) and 3 normal breaths (NB=3) are scored before step 416 occurs, MLEpoch equals (9/(9+3)) or 0.75.

In step 418, the calculated MLEpoch is compared against a threshold MLEpoch. In the illustrated example, the threshold MLEpoch equals 0.8. If the calculated MLEpoch is greater than or equal to 0.8, a mouth puff epoch signal is outputted by the controller 116 (step 420). If the calculated MLEpoch is less than 0.8, a normal breathing epoch signal is outputted by the controller 116 (step 422). It may be understood that the mouth puff epoch signal is generated if 80% or more of the breaths within the one-minute window represented by the timer T are determined to be mouth puff breaths, and that the normal breathing epoch signal is generated if less than 80% of the breaths within the one-minute window represented by the timer T are determined to be mouth puff breaths.

After either a mouth puff epoch signal or a normal breathing epoch signal is outputted, the method 400 loops such that step 401 is performed. T, ML, and NB are set to zero and step 402 is performed again.

Either the mouth puff signal generated in methods 200 or 300 with respect to FIG. 7 or 8 or the mouth puff epoch signal generated in method 400 with respect to FIG. 9 may be used in a number of ways. The controller 116 of the respiratory therapy system 100 may, upon determination or receipt of such signals, cause a message or alert to be outputted via the input/output module 118 (e.g. via a screen or speaker of the input/output module 118). The message or alert may comprise, for example but without limitation, a tone, a series of tones, speech, written text, or flashing lights. In some configurations, the message or alert may suggest that the patient should consider using a full-face mask or that the patient should visit a physician to diagnose the presence of mouth puff or mouth leak. The message or alert may be incorporated into a sleep report delivered to a physician.

In other configurations, the controller 116 of the respiratory therapy system 100 may, upon determination or receipt of such signals, cause the flow generator 102 to decrease the pressure or flow rate of the gas flow delivered to the patient. Decreasing the pressure or flow rate of the gas flow delivered can reduce drying out of the oral mucosa that can occur when flow leaks from the mouth.

In still other configurations, the controller 116 of the respiratory therapy system 100 may, upon the determination or receipt of such signals, cause the humidifier 108 to increase the humidity of the gas flow delivered to the patient. Increasing the humidity content of the gas flow delivered can also reduce drying out of the oral mucosa that can occur when flow leaks from the mouth.

Some preferred features:

Paragraph 1. A respiratory event determination system comprising a controller configured to determine a presence of a respiratory event as a function of a sub-window of an expiratory window of a breath, wherein the expiratory window extends between a first time $t_1$ and a second time $t_2$, and wherein the sub-window is limited to a portion of the expiratory window extending between a third time $t_3$ and a fourth time $t_4$, the third time $t_3$ being after the first time $t_1$ and/or the fourth time $t_4$ being before the second time $t_2$.

Paragraph 2. The respiratory event determination system of Paragraph 1, wherein the third time $t_3$ is after the first time $t_1$ and the fourth time $t_4$ is before the second time $t_2$.

Paragraph 3. The respiratory event determination system of either of Paragraphs 1 or 2, wherein the third time $t_3$ lies in the range of about 5% to about 35% of the time between the first time $t_1$ and the second time $t_2$.

Paragraph 4. The respiratory event determination system of any one of Paragraphs 1-3, wherein the third time $t_3$ is at about 20% of the time between the first time $t_1$ and the second time $t_2$.

Paragraph 5. The respiratory event determination system of any one of Paragraphs 1-4, wherein the fourth time $t_4$ lies in the range of about 65% to about 95% of the time between the first time $t_1$ and the second time $t_2$.

Paragraph 6. The respiratory event determination system of any one of Paragraphs 1-5, wherein the fourth time $t_4$ is at about 80% of the time between the first time $t_1$ and the second time $t_2$.

Paragraph 7. The respiratory event determination system of any one of Paragraphs 1-6, wherein the third time $t_3$ is selected such that it is a function of a characteristic of the breath.

Paragraph 8. The respiratory event determination system of any one of Paragraphs 1-7, wherein the third time $t_3$ is selected such that it is a function of a zero-crossing of a derivative of the expiratory window.

Paragraph 9. The respiratory event determination system of Paragraph 8, wherein the third time $t_3$ is selected such that it is contemporaneous or about contemporaneous with a zero-crossing of a derivative of the expiratory window.

Paragraph 10. The respiratory event determination system of either one of Paragraphs 8 or 9, wherein the derivative of the expiratory window is the first derivative of the expiratory window.

Paragraph 11. The respiratory event determination system of any one of Paragraphs 8-10, wherein the zero-crossing is a first zero-crossing.

Paragraph 12. The respiratory event determination system of any one of Paragraphs 8-10, wherein the zero-crossing is a second zero-crossing.

Paragraph 13. The respiratory event determination system of either of Paragraphs 7 or 8, wherein the function is a piecewise function.

Paragraph 14. The respiratory event determination system of Paragraph 13, wherein the piecewise function is such that the third time $t_3$ is selected such that it is set to a fifth time $t_5$ that is contemporaneous or about contemporaneous with a time $t_{zc1}$ of a first or second zero-crossing of a first derivative of the expiratory window if the time $t_{zc1}$ of the first or second zero-crossing is less than, or less than or equal to a first threshold time $t_{th1}$ between the first time $t_1$ and the second time $t_2$, and such that it is set to a sixth time $t_6$ if the time $t_{zc1}$ of the first or second zero-crossing is greater than or equal to, or greater than the first threshold time $t_{th1}$ between the first time $t_1$ and the second time $t_2$.

Paragraph 15. The respiratory event determination system of Paragraph 14, wherein the sixth time $t_6$ is earlier than the first threshold time $t_{th1}$.

Paragraph 16. The respiratory event determination system of either one of Paragraphs 14 or 15, wherein the sixth time $t_6$ lies in the range of about 5% to about 35% of the time between the first time $t_1$ and the second time $t_2$.

Paragraph 17. The respiratory event determination system of any one of Paragraphs 14-16, wherein the sixth time $t_6$ is at about 20% of the time between the first time $t_1$ and the second time $t_2$.

Paragraph 18. The respiratory event determination system of any one of Paragraphs 14-17, wherein the first threshold time $t_{th1}$ is a predetermined time between the first time $t_1$ and the second time $t_2$.

Paragraph 19. The respiratory event determination system of any one of Paragraphs 1-18, wherein the fourth time $t_4$ is selected as a function of a characteristic of the breath.

Paragraph 20. The respiratory event determination system of any one of Paragraphs 1-19, wherein the fourth time $t_4$ is selected such that it is a function of a zero-crossing of a derivative of the expiratory window.

Paragraph 21. The respiratory event determination system of Paragraph 20, wherein the fourth time $t_4$ is selected such that it is contemporaneous or about contemporaneous with a zero-crossing of a derivative of the expiratory window.

Paragraph 22. The respiratory event determination system of either one of Paragraphs 20 or 21, wherein the derivative is a first derivative of the expiratory window.

Paragraph 23. The respiratory event determination system of any one of Paragraphs 20-22, wherein the zero-crossing is a last zero-crossing.

Paragraph 24. The respiratory event determination system of either of Paragraphs 19 or 20, wherein the function is a piecewise function.

Paragraph 25. The respiratory event determination system of Paragraph 24, wherein the piecewise function is such that the fourth time $t_4$ is selected such that it is set to a seventh time $t_7$ that is contemporaneous or about contemporaneous with a time $t_{zc2}$ of a last zero-crossing of the first derivative of the expiratory window if the time $t_{zc2}$ of the last zero-crossing is greater than or equal to, or greater than, a second threshold time $t_{th2}$ between the first time $t_1$ and the second time $t_2$, and such that it is set to an eighth time $t_8$ if the time $t_{zc2}$ of the first or second zero-crossing is less than, or less than or equal to, the second threshold time $t_{th2}$ between the first time $t_1$ and the second time $t_2$.

Paragraph 26. The respiratory event determination system of Paragraph 25, wherein the eighth time $t_8$ is greater than the second threshold time $t_{th2}$.

Paragraph 27. The respiratory event determination system of either of Paragraphs 25 or 26, wherein the eighth time $t_8$ lies in the range of about 65% to about 95% of the time between the first time $t_1$ and the second time $t_2$.

Paragraph 28. The respiratory event determination system of any one of Paragraphs 25-27, wherein the eighth time $t_8$ is at about 80% of the time between the first time $t_1$ and the second time $t_2$.

Paragraph 29. The respiratory event determination system of any one of Paragraphs 25-28, wherein the second threshold time $t_{th2}$ is a predetermined time between the first time $t_1$ and the second time $t_2$.

Paragraph 30. The respiratory event determination system of any one of Paragraphs 1-29, wherein the respiratory event comprises a mouth puff event.

Paragraph 31. The respiratory event determination system of any one of Paragraphs 1-30, wherein the controller is further configured to generate a non-event determination signal if a linear regression slope of the expiratory window between the third time $t_3$ and the fourth time $t_4$ is greater than a respiratory event slope threshold $res_t$.

Paragraph 32. The respiratory event determination system of any one of Paragraphs 1-31, wherein the controller is further configured to generate an event determination signal if a linear regression slope of the expiratory window between the third time $t_3$ and the fourth time $t_4$ is less than or equal to a respiratory event slope threshold $res_t$.

Paragraph 33. The respiratory event determination system of any one of Paragraphs 1-32, wherein the controller is further configured to generate a determination signal ds upon determination of the presence of a respiratory event, and generate an event epoch signal if the determination signal is present for at least a first time period $tp_1$ within a second time period $tp_2$.

Paragraph 34. The respiratory event determination system of any one of Paragraphs 1-32, wherein the controller is further configured to generate a determination signal ds upon determination of the presence of a respiratory event, and generate an event epoch signal if the determination signal is present for at least a first number of breaths $tb_1$ within a second number of breaths $tb_2$.

Paragraph 35. A respiratory event determination system comprising a controller configured to determine a presence of a respiratory event as a function of a sub-window of an expiratory window of a breath, wherein the expiratory window extends between a first time $t_1$ and a second time $t_2$, and wherein the sub-window is limited to a portion of the expiratory window extending between a third time $t_3$ and a fourth time $t_4$, and wherein the third time $t_3$ is a function of a time of a first or second zero-crossing of a first derivative of the expiratory window.

Paragraph 36. The respiratory event determination system of Paragraph 35, wherein the third time $t_3$ is contemporaneous or about contemporaneous with the first or second zero-crossing of the first derivative of the expiratory window.

Paragraph 37. The respiratory event determination system of either one of Paragraphs 35-36, wherein the fourth time $t_4$ is a function of a time of a last zero-crossing of a first derivative of the expiratory window.

Paragraph 38. The respiratory event determination system of Paragraph 37, wherein the fourth time $t_4$ is contemporaneous or about contemporaneous with the last zero-crossing of the first derivative of the expiratory window.

Paragraph 39. A respiratory event determination system comprising a controller configured to determine a presence of a respiratory event as a function of a sub-window of an expiratory window of a breath, wherein the expiratory window extends between a first time $t_1$ and a second time $t_2$, and wherein the sub-window is limited to a portion of the expiratory window extending between a third time $t_3$ and a fourth time $t_4$, and wherein the fourth time $t_3$ is a function of a time of a last zero-crossing of a first derivative of the expiratory window.

Paragraph 40. The respiratory event determination system of Paragraph 39, wherein the fourth time $t_4$ is contemporaneous or about contemporaneous with the last zero-crossing of the first derivative of the expiratory window.

Paragraph 41. A method of using the respiratory event determination system of any one of Paragraphs 1-40 to determine the presence of a respiratory event.

Paragraph 42. The method of Paragraph 41, wherein the respiratory event is a mouth puff event.

Paragraph 43. A respiratory therapy system comprising a respiratory event determination system according to any one of Paragraphs 1-40.

Paragraph 44. The respiratory therapy system of Paragraph 43, further comprising a flow generator.

Paragraph 45. The respiratory therapy system of Paragraph 44, wherein the flow generator is a PAP apparatus.

Paragraph 46. The respiratory therapy system of either of Paragraphs 44 or 45, wherein the controller is further configured to adjust a pressure and/or flow rate of gases generated by the flow generator as a function of the determined presence or non-presence of the respiratory event.

Paragraph 47. The respiratory therapy system of Paragraph 46, wherein the respiratory event is a mouth puff event.

Paragraph 48. The respiratory therapy system of Paragraph 47, wherein the pressure and/or flow rate of gases generated by the flow generator is decreased upon determination of the mouth puff event.

Paragraph 49. The respiratory therapy system of any one of Paragraphs 43-48, further comprising a humidifier.

Paragraph 50. The respiratory therapy system of Paragraph 49, wherein the controller is further configured to adjust an output humidity of the humidifier as a function of the determined presence or non-presence of the respiratory event.

Paragraph 51. The respiratory therapy system of Paragraph 50, wherein the respiratory event is a mouth puff event.

Paragraph 52. The respiratory therapy system of Paragraph 51, wherein the output humidity of the humidifier is increased upon determination of the mouth puff event.

Paragraph 53. The respiratory therapy system of any one of Paragraphs 43-52, further comprising a sealing patient interface.

Paragraph 54. The respiratory therapy system of Paragraph 53, further comprising a gas delivery conduit that links the flow generator to the sealing patient interface.

Paragraph 55. A breath monitoring system substantially as shown and described with reference to the accompanying figures.

Paragraph 56. A respiratory therapy system substantially as shown and described with reference to the accompanying figures.

Paragraph 57. A PAP apparatus substantially as shown and described with reference to the accompanying figures.

Paragraph 58. A method of determining the presence of a respiratory event substantially as shown and described with reference to the accompanying figures.

Paragraph 59. A method of determining the presence of mouth puff, determining the presence of a mouth puff event, or determining the presence of a mouth puff epoch event substantially as shown and described with reference to the accompanying figures.

Paragraph 60. A mouth puff determination system comprising a controller configured to determine a presence of a respiratory event as a function of a sub-window of an expiratory window of a breath, wherein the expiratory window extends between a first time $t_1$ and a second time $t_2$, and wherein the sub-window is limited to a portion of the expiratory window extending between a third time $t_3$ and a fourth time $t_4$, the fourth time $t_4$ being before the second time $t_2$.

Paragraph 61. A method of determining the presence of a respiratory event, comprising analyzing the output of a function of a sub-window of an expiratory window of a breath, wherein the expiratory window extends between a first time $t_1$ and a second time $t_2$, and wherein the sub-window is limited to a portion of the expiratory window extending between a third time $t_3$ and a fourth time $t_4$, the fourth time $t_4$ being before the second time $t_2$.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Language of degree used herein, such as the terms "approximately," "about," "generally," and "substantially," as used herein represent a value, amount or characteristic close to the stated value, amount or characteristic that still performs a desired function or achieves a desired result. The deviation from the stated value, amount or characteristic could, for example, reflect acceptable tolerances, conversion factors, rounding off, measurement error, or other factors known to those of skill in the art. For example, the terms "generally parallel" and "substantially parallel" refer to a value, amount or characteristic that can depart from exactly parallel by less than or equal to 15 degrees, 10 degrees, 5 degrees, 3 degrees, 1 degree, 0.1 degree, or otherwise.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A respiratory therapy system for delivering a flow of gases to a patient, the respiratory therapy system comprising:
    a flow sensor configured to generate a flow signal based at least in part on gas flow within the respiratory therapy system;
    a controller in electronic communication with the flow sensor, wherein the controller is configured to:
        determine a presence of a respiratory event as a function of the flow signal within a sub-window of an expiratory window of a breath, wherein the expiratory window extends between a first time $t_1$ and a second time $t_2$, and wherein the sub-window is limited to a portion of the expiratory window extending between a third time $t_3$ and a fourth time $t_4$, the third time $t_3$ being after the first time $t_1$,
        select the third time $t_3$ as a piecewise function of a characteristic of the breath, wherein the characteristic of the breath is a parameter of the flow signal within the expiratory window, wherein the piecewise function is configured such that the third time $t_3$ is selected such that it is a function of a zero-crossing of a derivative of the flow signal within the expiratory window.

2. The respiratory therapy system of claim 1, wherein the third time $t_3$ is selected such that it lies in the range of about 5% to about 35% of the time between the first time $t_1$ and the second time $t_2$.

3. The respiratory therapy system of claim 1, wherein the third time $t_3$ is set to a fifth time $t_5$ that is selected such that it is contemporaneous or about contemporaneous with the zero-crossing of a derivative of the flow signal within the expiratory window.

4. The respiratory therapy system of claim 1, wherein the piecewise function is such that the third time $t_3$ is selected such that it is set to a fifth time $t_5$ that is contemporaneous or about contemporaneous with a time $t_{zc1}$ of a first or second zero-crossing of a first derivative of the flow signal within the expiratory window if the time $t_{zc1}$ of the first or second zero-crossing is less than or equal to a first threshold time $t_{th1}$ between the first time $t_1$ and the second time $t_2$, and such that it is set to a sixth time $t_6$ if the time $t_{zc1}$ of the first or second zero-crossing is greater than or equal to the first threshold time $t_{th1}$ between the first time $t_1$ and the second time $t_2$.

5. The respiratory therapy system of claim 4, wherein the sixth time $t_6$ is earlier than the first threshold time $t_{th1}$.

6. The respiratory therapy system of claim 4, wherein the sixth time $t_6$ lies in the range of about 5% to about 35% of the time between the first time $t_1$ and the second time $t_2$.

7. The respiratory therapy system of claim 4, wherein the sixth time $t_6$ is at about 20% of the time between the first time $t_1$ and the second time $t_2$.

8. The respiratory therapy system of claim 1, wherein the respiratory event comprises a mouth puff event.

9. A respiratory therapy system for delivering a flow of gases to a patient, the respiratory therapy system comprising:
    a flow sensor configured to generate a flow signal based at least in part on gas flow within the respiratory therapy system;
    a controller in electronic communication with the flow sensor, wherein the controller is configured to:
        determine a presence of a respiratory event as a function of the flow signal within a sub-window of an expiratory window of a breath, wherein the expiratory window extends between a first time $t_1$ and a second time $t_2$, and wherein the sub-window is limited to a portion of the expiratory window extending between a third time $t_3$ and a fourth time $t_4$, the fourth time $t_4$ being before the second time $t_2$,
        select the fourth time $t_4$ as a piecewise function of a characteristic of the breath, wherein the characteristic of the breath is a parameter of the flow signal within the expiratory window, wherein the piecewise function is configured such that the fourth time $t_4$ is selected such that it is a function of a zero-crossing of a derivative of the flow signal within the expiratory window.

10. The respiratory therapy system of claim 9, wherein the fourth time $t_4$ is selected such that it lies in the range of about 65% to about 95% of the time between the first time $t_1$ and the second time $t_2$.

11. The respiratory therapy system of claim 9, wherein the fourth time $t_4$ is set to a seventh time $t_7$ that is selected such that it is contemporaneous or about contemporaneous with a zero-crossing of a derivative of the flow signal within the expiratory window.

12. The respiratory therapy system of claim 9, wherein the piecewise function is such that the fourth time $t_4$ is selected such that it is set to a seventh time $t_7$ that is contemporaneous or about contemporaneous with a time $t_{zc2}$ of a last zero-crossing of the first derivative of the flow signal within the expiratory window if the time $t_{zc2}$ of the last zero-crossing is greater than or equal to a second threshold time $t_{th2}$ between the first time $t_1$ and the second time $t_2$, and such that it is set to an eighth time $t_8$ if the time $t_{zc2}$ of the last zero-crossing is less than or equal to the second threshold time $t_{th2}$ between the first time $t_1$ and the second time $t_2$.

13. The respiratory therapy system of claim 12, wherein the eighth time $t_8$ is greater than the second threshold time $t_{th2}$.

14. The respiratory therapy system of claim 12, wherein the eighth time $t_8$ lies in the range of about 65% to about 95% of the time between the first time $t_1$ and the second time $t_2$.

15. The respiratory therapy system of claim 12, wherein the eighth time $t_8$ is at about 80% of the time between the first time $t_1$ and the second time $t_2$.

16. The respiratory therapy system of claim 9, wherein a respiratory event comprises a mouth puff event.

* * * * *